(12) United States Patent
Gwozdz

(10) Patent No.: US 10,039,830 B2
(45) Date of Patent: Aug. 7, 2018

(54) TOPICAL ANESTHETIC COMPOSITION

(71) Applicant: CETYLITE INDUSTRIES, INC., Pennsauken, NJ (US)

(72) Inventor: Garry Gwozdz, Jim Thorpe, PA (US)

(73) Assignee: CETYLITE INDUSTRIES, INC., Pennsauken, NJ (US)

( * ) Notice: Subject to any disclaimer, the term of this patent is extended or adjusted under 35 U.S.C. 154(b) by 197 days.

(21) Appl. No.: 15/061,281

(22) Filed: Mar. 4, 2016

(65) Prior Publication Data

US 2017/0252445 A1    Sep. 7, 2017

(51) Int. Cl.
| | |
|---|---|
| *A61K 31/245* | (2006.01) |
| *A61K 47/10* | (2017.01) |
| *A61M 11/00* | (2006.01) |
| *A61C 19/08* | (2006.01) |
| *A61K 9/00* | (2006.01) |
| *A61K 47/26* | (2006.01) |
| *A61M 19/00* | (2006.01) |

(52) U.S. Cl.
CPC .............. *A61K 47/10* (2013.01); *A61C 19/08* (2013.01); *A61K 9/0063* (2013.01); *A61K 31/245* (2013.01); *A61K 47/26* (2013.01); *A61M 11/007* (2014.02); *A61M 19/00* (2013.01)

(58) Field of Classification Search
CPC .... A61K 31/245; A61K 47/10; A61K 9/0063; A61K 8/04
See application file for complete search history.

(56) References Cited

U.S. PATENT DOCUMENTS

| | | | |
|---|---|---|---|
| 4,052,513 A | 10/1977 | Kaplan | |
| 4,344,965 A | 8/1982 | Stone | |
| 4,529,601 A | 7/1985 | Broberg et al. | |
| 4,600,575 A | 7/1986 | Lin et al. | |
| 5,002,974 A | 3/1991 | Geria | |
| 5,332,576 A | 7/1994 | Mantelle | |
| 5,446,063 A | 8/1995 | Reuter et al. | |
| 5,563,153 A | 10/1996 | Mueller et al. | |
| 5,585,398 A | 12/1996 | Ernst | |
| 5,618,515 A | 4/1997 | Singh et al. | |
| 5,760,077 A | 6/1998 | Shahinian, Jr. | |
| 5,993,836 A | 11/1999 | Castillo | |
| 6,114,344 A | 9/2000 | Druzgala et al. | |
| 6,187,294 B1 | 2/2001 | Penner | |
| 6,299,902 B1 | 10/2001 | Jun et al. | |
| 6,391,888 B1 | 5/2002 | Gleich | |
| 6,413,496 B1 | 7/2002 | Goodman et al. | |
| 6,413,499 B1 | 7/2002 | Clay | |
| 6,894,078 B2 | 5/2005 | Castillo | |
| 7,273,887 B1 | 9/2007 | Wepfer | |
| 7,695,733 B2 | 4/2010 | Zasler et al. | |
| 7,763,653 B2 | 7/2010 | Pacheco et al. | |
| 7,883,488 B2 | 2/2011 | Shantha et al. | |
| 8,119,694 B2 | 2/2012 | Campbell et al. | |
| 8,367,703 B2 | 2/2013 | Jones | |
| 8,523,569 B2 | 9/2013 | Neshat | |
| 8,580,282 B2* | 11/2013 | Kollar ................ | A61K 9/0043 424/400 |
| 8,876,794 B2 | 11/2014 | Xia | |
| 8,960,128 B2 | 2/2015 | Sheil et al. | |
| 8,968,710 B1 | 3/2015 | Wickenhauser et al. | |
| 2005/0014823 A1 | 1/2005 | Soderlund et al. | |
| 2005/0085791 A1 | 4/2005 | Shaw et al. | |
| 2005/0123484 A1* | 6/2005 | Hirsh ..................... | A61K 9/12 424/45 |
| 2005/0137177 A1 | 6/2005 | Shafer | |
| 2006/0079558 A1 | 4/2006 | Aberg et al. | |
| 2006/0222687 A1 | 10/2006 | Carter et al. | |
| 2007/0048338 A1 | 3/2007 | Ladd | |
| 2008/0214664 A1 | 9/2008 | Spengler et al. | |
| 2008/0268050 A1 | 10/2008 | Gerrish et al. | |
| 2010/0305130 A1 | 12/2010 | Phillips | |
| 2011/0052738 A1 | 3/2011 | Bennett | |
| 2011/0288123 A1 | 11/2011 | Kisak et al. | |

(Continued)

FOREIGN PATENT DOCUMENTS

| | | |
|---|---|---|
| WO | WO-96/14828 A1 | 5/1996 |
| WO | WO-2004/103264 A2 | 12/2004 |

(Continued)

OTHER PUBLICATIONS

Adriani et al., "Mixtures of Local Anesthetics, the Effectiveness of Combination of Benzocaine Butamben, and Tetracaine Topically," Anesthesiology Review, vol. VIII, No. 12, pp. 15-19, Dec. 1981.
Benzocaine—Official Monographs, "Benzocaine, Butamben and Tetracaine Hydrochloride Topical Solution", p. 232.
Cetylite® Safety Data Sheet—Cetacaine, Sep. 23, 2015.
Prescribing Information, Cetacaine Topical Anesthetic, Dec. 8, 2015, http://www.cetacaine.com/dental/about/prescribing-information.
Dentsply Material Safety Data Sheet, Oraqix. Created Jul. 11, 2013.

(Continued)

*Primary Examiner* — Lakshmi S Channavajjala
(74) *Attorney, Agent, or Firm* — Polsinelli PC

(57) ABSTRACT

A topical anesthetic composition comprising benzocaine, pharmaceutically acceptable salt thereof, amide thereof and/or ester thereof; tetracaine and/or pharmaceutically acceptable salt thereof; ethanol; polyethylene glycol; propylene glycol; water; and benzyl alcohol is provided. Also provided is method for dispensing the above topical anesthetic composition to a desired site such by spraying the topical anesthetic from a pump actuated metered dose spray device. The topical anesthetic composition can also be administered subgingivally with a syringe and applicator tip. A product comprising the above topical anesthetic spray composition contained in a pump actuated metered dose spray device.

31 Claims, No Drawings

(56) References Cited

U.S. PATENT DOCUMENTS

| | | |
|---|---|---|
| 2012/0004303 A1 | 1/2012 | Benson et al. |
| 2014/0162958 A1 | 6/2014 | Robbins |
| 2014/0348959 A1 | 11/2014 | Mitchnick et al. |
| 2015/0018387 A1 | 1/2015 | Campbell et al. |

FOREIGN PATENT DOCUMENTS

| | | |
|---|---|---|
| WO | WO-2007/103555 A2 | 9/2007 |
| WO | WO-2010/005400 A1 | 1/2010 |
| WO | WO-2015/021387 A2 | 2/2015 |

OTHER PUBLICATIONS

Product Monograph—EMLA® Crean, EMLA® Patch, Lidocaine 2.5% and Prilocaine 2.5%, Cream and Patch, Topical Anesthetic for Dermal Analgesia, Astraseneca Canada Inc., May 25, 2010, pp. 1-46.

International Search Report and Written Opinion of PCT/US17/20411 dated May 19, 2017.

* cited by examiner

TOPICAL ANESTHETIC COMPOSITION

TECHNICAL FIELD

The present disclosure relates to a topical anesthetic composition comprising benzocaine and/or a derivative thereof, and tetracaine and/or derivative thereof; and a particular combination of diluents. The topical anesthetic composition according to the present disclosure can be sprayed such as using a metered dose pump device and is free from propellants.

BACKGROUND

A number of aerosol formulations containing pharmaceutical products (both metered and non-metered) exist. However, most of these products contain chlorinated fluorocarbon propellants (CFCs), both individually and in combinations. With the advent of the Montreal protocols, many countries of the world agreed to reduce the use of is "greenhouse effect gases". CFCs are major contributors to this problem.

Reformulation of topical anesthetic spray compositions to exclude the chlorinated fluorocarbon propellants and still provide an acceptable topical anesthetic spray composition has faced many challenging problems and especially compositions with benzocaine and tetracaine. Along these lines, active benzocaine and tetracaine components need to be dissolved in the composition and exhibit stability over extend periods of time and temperature changes. When the compositions are to be administered by spraying, the compositions must have a viscosity that is low enough for spraying. These properties compete (i.e.-contradictory to each other) with each other making it difficult to find alternative compositions.

The problems are further exacerbated when the composition is to be free from propellants and to minimize the amount of highly volatile components such as ethanol and isopropyl alcohol.

Yet another problem with some current formulations is degradation of the product during packaging.

SUMMARY OF DISCLOSURE

The present disclosure is concerned with a topical anesthetic composition comprising:
A. benzocaine, pharmaceutically acceptable salt thereof, amide thereof and/or ester thereof in an amount of about 10% to about 20% by weight;
B. tetracaine and/or pharmaceutically acceptable salt thereof in an amount of about 1% to about 5% by weight;
C. ethanol in an amount of about 5% to about 20% by weight;
D. polyethylene glycol and/or polypropylene glycol in an amount of about 20 to about 35% by weight;
E. propylene glycol in an amount of about 10% to about 30% by weight;
F. water in an amount of about 5% to about 30% by weight; and
G. benzyl alcohol in an amount of about 1% to about 10% by weight;
and the amounts of A to G are based upon the total amount of A to G in the composition.

The polyethylene glycol and polypropylene glycol typically have a weight average molecular weight ($M_w$) of at least about 100, more typically about 100 to about 700 and preferably is polyethylene glycol 300.

The present disclosure also relates to a method of using the above disclosed topical anesthetic which comprising applying the topical anesthetic to a desired site of an individual.

Another aspect of the present disclosure relates to a method for dispensing the above disclosed topical anesthetic to a desired site of an individual by spraying the topical anesthetic from a pump actuated metered dose spray device.

Moreover, the present disclosure relates to a product comprising the above disclosed topical anesthetic composition contained in a pump actuated metered dose spray device.

Still other objects and advantages of the present disclosure will become readily apparent by those skilled in the art from the following detailed description, wherein it is shown and described preferred embodiments, simply by way of illustration of the best mode contemplated. As will be realized, the disclosure is capable of other and different is embodiments, and its several details are capable of modifications in various obvious respects, without departing from the disclosure. Accordingly, the description is to be regarded as illustrative in nature and not as restrictive.

BEST AND VARIOUS MODES

The topical anesthetic spray compositions according to the present disclosure comprise a benzocaine component. The benzocaine component can be benzocaine, a pharmaceutically acceptable salt thereof, a pharmaceutically acceptable amide thereof or a pharmaceutically acceptable ester thereof. The amount of the benzocaine component is typically about 10% to about 20% by weight and according to one embodiment is about 14% by weight.

The compositions of the present disclosure also include tetracaine and/or a pharmaceutically acceptable salt thereof. The amount of the tetracaine and/or pharmaceutically acceptable salt thereof is typically about 1% to about 5% by weight and according to one embodiment is about 2% by weight.

Pharmaceutically acceptable salts of the anesthetic agents employed according to the present disclosure include those derived from pharmaceutically acceptable, inorganic and organic acids and bases. Examples of suitable acids include hydrochloric, hydrobromic, sulphuric, nitric, perchloric, fumaric, maleic, phosphoric, glycollic, lactic, salicyclic, succinic, toluene-p-sulphonic, tartaric, acetic, citric, methanesulphonic, formic, benzoic, malonic, naphthalene-2-sulphonic, trifluoroacetic and benzenesulphonic acids.

Salts derived from appropriate bases include alkali such as sodium and ammonia.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The compositions according to the present disclosure also comprise ethanol. The amount of the ethanol is typically about 5% to about 20% by weight, more typically 10% to 15% by weight and according to one embodiment is about is about 10 to about 12% by weight.

The compositions according to the present disclosure also comprise polyethylene glycol and/or polypropylene glycol is typically about 20% to about 35% by weight, more typically about 25% to about 30% by weight and according to one embodiment is about 29 to about 30% by weight.

The polyethylene glycol and polypropylene glycol typically have a weight average molecular weight ($M_w$) of at least about 100, more typically about 100 to about 700 and preferably is polyethylene glycol 300.

The compositions according to the present disclosure also comprise propylene glycol. The amount of the propylene glycol is typically about 10% to about 30% by s weight, more typically about 10% to about 25% by weight and according to one embodiment is about is about 13 to about 22.5% by weight.

The compositions according to the present disclosure also comprise ethanol. The amount of the ethanol is typically about 10% to about 20% by weight, more typically about 10% to about 15% by weight and according to one embodiment is about 10 to about 12% by weight.

The compositions according to the present disclosure further contain water. The amount of the water is typically about 5% to about 30% by weight, more typically about 10% to about 25% by weight and according to one embodiment is about 15% to about 23.5% by weight.

Furthermore, the compositions according to the present disclosure also include benzyl alcohol. The amount of the benzyl alcohol is typically about 1% to about 10% by weight and according to one embodiment is about 5% by weight.

The above amounts of the benzocaine component, tetracaine component, polyethylene glycol, propylene glycol, ethanol, water and benzyl alcohol are based upon the total of the benzocaine component, tetracaine component, polyethylene glycol, polypropylene glycol, propylene glycol, ethanol, water and benzyl alcohol in the composition.

The compositions according to the present disclosure when to be administered by spraying using typical commercially available spray devices and especially metered spray devices typically have a maximum viscosity of about 25 and more typically a maximum of about 20 centipoise, a particular example being about 15 centipoise.

The compositions according to the present disclosure typically have a pH of about 6.2 to about 7.4.

In addition, if desired, the compositions of the present invention can include s auxiliary aesthetic agents such as butamben and pharmaceutically acceptable salts thereof. When present, such anesthetic agents are typically present in amounts such that the auxiliary aesthetic agents are solubilized in the compositions and typically is about 0.1 to about 10%, and more typically about 1 to about 5% by weight.

The compositions of the present disclosure can include other auxiliary additives such as surfactants, preservatives and flavoring agents. When present, such is typically present in amounts of about 0.1 to about 5% by weight and more typically about 0.1 to about 1% by weight.

Formulations may be prepared using a pharmaceutically acceptable auxiliary components composed of materials that are considered safe and effective and may be administered to an individual without causing undesirable biological side effects or unwanted interactions. As generally used herein "auxiliary components" include, but is not limited to sweetening agents, flavorants and preservatives. Suitable auxiliary components including sweetening agents such as saccharin and preservatives such as benzalkonium chloride and cetyldimethylammonium bromide can be added to this solution.

Flavorants can be synthetic or naturally occurring compounds. Suitable flavorants include, but are not limited to, anise oil, cinnamon oil, cocoa, menthol, orange oil, peppermint oil, and vanillin. Suitable sweetening agents include, but are not limited to, saccharin, aspartame, dextrose, glycerin, mannitol, sorbitol, and sucrose. In a preferred embodiment, sodium saccharin is used as a sweetening agent.

Preservatives are used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium s propionate, benzalkonium chloride, benzethonium chloride, benzyl alcohol, cetypyridinium chloride, chlorobutanol, phenol, phenylethyl alcohol, and thimerosal. Preservatives can also include antioxidants such a BHA, BHT, vitamin E, and other pharmacologically acceptable antioxidants.

In a preferred embodiment, benzalkonium chloride is used to reduce surface tension and improve atomization when sprayed.

The compositions according to the present disclosure do not include a propellant and are administered using a pump-actuated spray. In addition, according to the present disclosure, it is preferred that the composition be free or at least substantially free (e.g. is less than about 0.1% by weight) of dipropylene glycol, a preferred solvent used in many topical anesthetic spray composition.

The compositions of the present disclosure can be employed as metered non-aerosol sprays. The non-aerosol spray is administered as a liquid for the administration to all accessible mucous membranes (excluding the eyes) to control pain, itching, and gagging.

The non-aerosol is preferably administered in a pump actuated metered dose spray device. The spray can, with the metering device, will typically be a glass container (e.g. pharmaceutical grade glass bottle). The compositions according to the present disclosure can also be dispensed in single unit dose form.

The compositions according to the present disclosure can also be administered for instance using a syringe and applicator tip, for instance, in dental applications. In dental applications, the compositions according to the present disclosure can be used for scaling and root planning procedures. The compositions can be applied subgingivally with a syringe and applicator tip.

The following non-limiting examples are presented to further illustrate the present invention, wherein the amounts are weight/weight percent unless stated otherwise.

The viscosities of the formulations were determined using a TA Instrument Advanced Rheometer AR1000 Stress controlled rheometer. The measurements were made using a 60 mm acrylic plate geometry at a 1000 pm gap, and a set temperature of 25° C. The viscosity was measured against increasing applied shear stress from 0.01-50 Pa.

Delivered dose and informal spray pattern characterizations were performed. The delivered dose was measured by recording the starting weight of the spray container for each formulation, after the pump was fully primed, then spraying five times and averaging the weight difference of the container pre and post spraying.

The method used to characterize spray pattern was to place a piece of 15 cm diameter qualitative filter paper at a distance of 4 inches from the pump, actuating the sprayer, and then visually assessing the pattern. Spray patterns were rated as circular, irregular, oblong, semicircular, semi-oblong, where irregular is an indication of poor atomization resulting in a blotchy spray pattern. Also height and width of the spray patterns were measured.

Performance was assessed in a LMA MADomizer as well as additional metered dose pump actuated spray devices from Nemera and Aptar. Five replicates were performed for each combination of sprayer and formulation. All Nemera applicator heads were used with the Nemera SP3D200 pump and delivered, 200 mg of formulation per spray for each of the formulations evaluated. As per its stated 100 μL dose, the LMA MADomizer consistently delivered 100 mg of the formulations evaluated. The MADomizer would require two sprays to reach the target 200 mg dose. The Aptar actuator performed poorly since it visually displayed very large droplet size and an irregular spray pattern.

Examples 1-4 gave the most consistent performance for sprayability in both the Nemera and MADomizer sprayers, exhibiting mostly circular spray patterns. Example 4 gave a slightly smaller spray pattern size than the Examples 1-3, which were mostly comparable.

Additionally, it was noted that though the amount delivered was unaffected, the spray pattern was adversely affected for some of the applicators by decreasing the force used to actuate the pump.

The pH was measured using a 390pH/Temp/mV/ISE Meter

EXAMPLE 1

A composition containing 14% by weight of benzocaine, 2% by weight of tetracaine hydrochloride, 16.9% by weight of propylene glycol, 5% by weight of benzyl alcohol, 12% by weight of ethyl alcohol, 18% by weight of water, 29.7% by weight of polyethylene glycol 300, 0.5% by weight of benzalkonium chloride, 1.4% by weight of sodium saccharin, and 0.5% by weight of banana flavor was prepared. The formulation has a viscosity of 13.7 centipoise and pH of 4.92 and exhibited a circular spray pattern.

This composition was subjected to temperature cycling tests to determine its freezing behavior. The composition was placed into -20° C. freezer for approximately 19 hours, then removed and placed on the bench top undisturbed for 2 hours and 15 minutes until its temperature was close to room temperature range (22° C.-25° C.). The temperatures were measured using an infrared thermometer. The sample was then hand shaken for 5 seconds approximately every 3-5 minutes until the precipitate re-dissolved. The entire time for these formulations to reach room temperature and become clear solutions was approximately 2 hours and 50 minutes.

EXAMPLE 2

A composition containing 14% by weight of benzocaine, 2% by weight of tetracaine hydrochloride, 18.9% by weight of propylene glycol, 5% by weight of benzyl alcohol, 10% by weight of ethyl alcohol, 18% by weight of water, 29.7% by weight of polyethylene glycol 300, 0.5% by weight of benzalkonium chloride, 1.4% by weight of sodium saccharin, and 0.5% by weight of banana flavor was prepared. The formulation has a viscosity of 16.5 centipoise and pH of 4.99 and exhibited a circular spray pattern.

This composition was subjected to temperature cycling tests in the same manner as for Example 1. The composition exhibited somewhat greater precipitated solids during the test than did the composition of Example, but the time for all solids to return into solution was essentially the same as in Example 1.

EXAMPLE 3

A composition containing 14% by weight of benzocaine, 2% by weight of is tetracaine hydrochloride, 16.9% by weight of propylene glycol, 5% by weight of benzyl alcohol, 10% by weight of ethyl alcohol, 20% by weight of water, 29.7% by weight of polyethylene glycol 300, 0.5% by weight of benzalkonium chloride, 1.4% by weight of sodium saccharin, and 0.5% by weight of banana flavor was prepared. The formulation has a viscosity of 15.5 centipoise and pH of 4.91 and exhibited a circular spray pattern.

Temperature cycling was performed with the composition of this Example, wherein the formulation was placed into a circulating chiller bath and monitored for physical changes as the temperature was ramped down from 15° C. to 0° C. over several hours. The composition was then placed into a refrigerator at about 0° C. for 18 hours and then removed to room temperature. The formulation showed visible precipitation. At approximately 30 minute intervals, the formulation was hand shaken for about 1 minute until all precipitate was judged to have re-dissolved. The composition returned to a clear solution after 3 hours 30 minutes.

The composition was then placed into a -18° C. freezer for 19 hours, then removed and left to sit undisturbed at room temperature for 1.5 hours. The composition was then s hand shaken for 1 minute approximately every hour and observed for residual precipitate. The composition returned to a clear solution after 4 hours.

EXAMPLE 4

A composition containing 14% by weight of benzocaine, 2% by weight of tetracaine hydrochloride, 13.9% by weight of propylene glycol, 5% by weight of benzyl alcohol, 10% by weight of ethyl alcohol, 23% by weight of water, 29.7% by weight of polyethylene glycol 300, 0.5% by weight of benzalkonium chloride, 1.4% by weight of sodium saccharin, and 0.5% by weight of mint flavor was prepared. The formulation has a viscosity of 15.1 centipoise and pH of 4.89 and exhibited a circular spray pattern.

EXAMPLE 5

A composition containing 14% by weight of benzocaine, 2% by weight of tetracaine hydrochloride, 13.9% by weight of propylene glycol, 5% by weight of benzyl alcohol, 10% by weight of ethyl alcohol, 23% by weight of water, 29.7% by weight of polyethylene glycol 300, 0.5% by weight of benzalkonium chloride, 1.4% by weight of sodium saccharin, and 0.5% by weight of banana flavor was prepared. The formulation has a viscosity of 15.1 centipoise and has a pH of 5.02.

A temperature cycling cycle was performed with this composition at conditions of -2° C. to 25° C. over a 5 day period. Precipitation of solids was observed from the low temperature, however the precipitate was found to re-dissolve with simple shaking after approximately two hours at room temperature, but there was a minimal amount of precipitate that was observed microscopically that did not re-dissolve under these conditions. However, it is unknown if the precipitate was the active components.

EXAMPLE 6

A composition containing 14% by weight of benzocaine, 2% by weight of tetracaine hydrochloride, 14.9% by weight of propylene glycol, 5% by weight of benzyl s alcohol, 10% by weight of ethyl alcohol, 22% by weight of water, 29.7% by weight of polyethylene glycol 300, 0.5% by weight of benzalkonium chloride, 1.4% by weight of sodium saccharin, and 0.5% by weight of banana flavor was prepared. The formulation has a viscosity of 15.6 centipoise and a pH of 5.0.

A temperature cycling cycle was performed with this composition at conditions of −2° C. to 25° C. over a 5 day period. Precipitation of solids was observed from the low temperature, however the precipitate was found to re-dissolve with simple shaking after approximately two hours at room temperature.

Temperature cycling was also performed with the composition of this Example, wherein the formulation was placed into a circulating chiller bath and monitored for physical changes as the temperature was ramped down from 15° C. to 0° C. over several hours. A small amount of precipitate was observed at the end of this phase of tye test.

The composition was then placed into a refrigerator at about 0° C. for 18 hours and then removed to room temperature. The formulation showed visible precipitation. At approximately 30 minute intervals, the formulation was hand shaken for about 1 minute until all precipitate was judged to have re-dissolved. The composition returned to a clear solution after 4 hours.

The composition was then placed into a −18° C. freezer for 19 hours, then removed and left to sit undisturbed at room temperature for 1.5 hours. The composition was then hand shaken for 1 minute approximately every hour and observed for residual precipitate. The composition returned to a clear solution after 4 hours and 30 minutes.

EXAMPLE 7

A composition containing 14% by weight of benzocaine, 2% by weight of tetracaine hydrochloride, 14.9% by weight of propylene glycol, 5% by weight of benzyl alcohol, 10% by weight of ethyl alcohol, 22% by weight of water, 29.7% by weight of s polyethylene glycol 300, 0.5% by weight of benzalkonium chloride, 1.4% by weight of sodium saccharin, and 0.5% by weight of mint flavor was prepared. The formulation has a viscosity of 15.6 centipoise and pH of 5.8.

EXAMPLE 8

A composition containing 14% by weight of benzocaine, 2% by weight of tetracaine hydrochloride, 22.4% by weight of propylene glycol, 5% by weight of benzyl alcohol, 10% by weight of ethyl alcohol, 15% by weight of water, 29.7% by weight of polyethylene glycol 300, 0.5% by weight of benzalkonium chloride, 1.4% by weight of sodium saccharin, and 0.5% by weight of mint flavor was prepared. The formulation has a viscosity of 16.7 centipoise and pH of 4.76.

EXAMPLE 9

A composition containing 14% by weight of benzocaine, 2% by weight of tetracaine hydrochloride, 21.4% by weight of propylene glycol, 5% by weight of benzyl alcohol, 10% by weight of ethyl alcohol, 15.5% by weight of water, 29.7% by weight of polyethylene glycol 300, 0.5% by weight of benzalkonium chloride, 1.4% by weight of sodium saccharin, and 0.5% by weight of mint flavor was prepared. The formulation has a viscosity of 17.0 centipoise and pH of 4.79.

COMPARATIVE EXAMPLE 1

A composition containing 14% by weight of benzocaine, 2% by weight of tetracaine hydrochloride, 61.5% by weight of propylene glycol, 5% by weight of benzyl alcohol, 5% by weight of ethyl alcohol, 11.1% by weight of water, and 1.4% by weight of sodium saccharin was prepared. However, the solids were not dissolved.

COMPARATIVE EXAMPLE 2

A composition containing 14% by weight of benzocaine, 2% by weight of s tetracaine hydrochloride, 61.5% by weight of propylene glycol, 1% by weight of benzyl alcohol, 9% by weight of ethyl alcohol, 11.1% by weight of water, and 1.4% by weight of sodium saccharin was prepared. However, the solids were not dissolved.

COMPARATIVE EXAMPLE 3

A composition containing 14% by weight of benzocaine, 2% by weight of tetracaine hydrochloride, 61.5% by weight of propylene glycol, 2% by weight of benzyl alcohol, 8% by weight of ethyl alcohol, 11.1% by weight of PEG 300, and 1.4% by weight of sodium saccharin was prepared. The solids dissolved, but the viscosity was 36.3 centipoise.

COMPARATIVE EXAMPLE 4

A composition containing 14% by weight of benzocaine, 2% by weight of tetracaine hydrochloride, 61.5% by weight of propylene glycol, 2% by weight of benzyl alcohol, 9.16% by weight of ethyl alcohol, 9.94% by weight of water, and 1.4% by weight of sodium saccharin was prepared. However, the solids were not dissolved.

COMPARATIVE EXAMPLE 5

A composition containing 14% by weight of benzocaine, 2% by weight of tetracaine hydrochloride, 61.5% by weight of propylene glycol, 5% by weight of benzyl alcohol, 5% by weight of ethyl alcohol, 3.10 8% by weight of water, 8% by weight of PEG 300, and 1.4% by weight of sodium saccharin was prepared. The solids dissolved, but the viscosity was 28.2 centipoise.

COMPARATIVE EXAMPLE 6

A composition containing 14% by weight of benzocaine, 2% by weight of tetracaine hydrochloride, 61.5% by weight of propylene glycol, 5% by weight of benzyl alcohol, 10% by weight of ethyl alcohol, 6.1% by weight of PEG 300, and 1.4% by s weight of sodium saccharin was prepared. The solids dissolved, but the viscosity was 26.6 centipoise.

Exemplary embodiments of the present disclosure include:
Embodiment A. A topical anesthetic composition comprising:
A. benzocaine, pharmaceutically acceptable salt thereof, amide thereof and/or ester thereof in an amount of about 10% to about 20% by weight;
B. tetracaine and/or pharmaceutically acceptable salt thereof in an amount of about 1% to about 5% by weight;
C. ethanol in an amount of about 5% to about 20% by weight;
D. polyethylene glycol and/or polypropylene glycol in an amount of about 20 to about 35% by weight;
E. propylene glycol in an amount of about 10% to about 30% by weight;
F. water in an amount of about 5% to about 30% by weight; and
G. benzyl alcohol in an amount of about 1% to about 10% by weight;

and the amounts of A to G are based upon the total amount of A to G in the composition.

Embodiment B. The topical anesthetic composition according to Embodiment A, wherein the amount of the benzocaine, pharmaceutically acceptable salt thereof, amide thereof and/or ester thereof is about 14% by weight.

Embodiment C. The topical anesthetic composition according to Embodiment A or B, wherein the amount of the tetracaine and/or pharmaceutically acceptable salt thereof is about 2% by weight.

Embodiment D. The topical anesthetic composition according to any one of Embodiments A, B or C, wherein the amount of the ethanol is about 10% to about 15% by weight.

Embodiment E. The topical anesthetic composition according to any one of Embodiments A, B or C, wherein the amount of the ethanol is about 10% to about 12% by weight.

Embodiment F. The topical anesthetic composition according to any one of Embodiments A, B, C or D, wherein the amount of the polyethylene glycol and/or polypropylene glycol is about 25% to about 30% by weight.

Embodiment G. The topical anesthetic composition according to any one of Embodiments A, B, C, D or E, wherein the amount of the polyethylene glycol and/or polypropylene glycol is about 29% to about 30% by weight.

Embodiment H. The topical anesthetic composition according to any one of Embodiments A, B, C, D, E, F or G, wherein the amount of the propylene glycol is about 10% to about 25% by weight.

Embodiment I. The topical anesthetic composition according to any one of Embodiments A, B, C, D, E, F or G, wherein the amount of the propylene glycol is about 13% to about 22.5% by weight.

Embodiment J. The topical anesthetic composition according to any one of Embodiments A, B, C, D, E, F, G, H or I, wherein the amount of the amount of the water is about 10% to about 25% by weight.

Embodiment K. The topical anesthetic composition according to any one of Embodiments A, B, C, D, E, F, G, H, or I, wherein the amount of the amount of the water is about 15% to about 23.5% by weight.

Embodiment L. The topical anesthetic composition according to any one of Embodiments A, B, C, D, E, F, G, H, I, J, or K, wherein the amount of the amount of the benzyl alcohol is about 5% by weight.

Embodiment M. A topical anesthetic composition comprising
A. benzocaine, pharmaceutically acceptable salt thereof, amide thereof and/or ester thereof in an amount of about 14% by weight;
B. tetracaine and/or pharmaceutically acceptable salt thereof in an amount of about 2% by weight;
C. ethanol in an amount of about 10 to about 12% by weight;
D. polyethylene glycol and/or polypropylene glycol in an amount of about 29 to about 30% by weight;
E. propylene glycol in an amount of about 13 to about 22.5% by weight;
F. water in an amount of about 15 to about 23.5% by weight; and
G. benzyl alcohol in an amount of about 5% by weight
the amounts of A to G are based upon the total amount of A to G in the composition.

Embodiment N. The topical anesthetic composition according to any one of Embodiments A, B, C, D, E, F, G, H, I, J, K, L, or M, wherein the polyethylene glycol and/or polypropylene glycol has a weight average molecular weight ($M_w$) of at least about 100.

Embodiment O. The topical anesthetic composition according to any one of Embodiments A, B, C, D, E, F, G, H, I, J, K, L, or M, wherein the polyethylene glycol and/or polypropylene glycol has a weight average molecular weight ($M_w$) of about 100 to about 700.

Embodiment P. The topical anesthetic composition according to any one of Embodiments A, B, C, D, E, F, G, H, I, J, K, L, or M, wherein the polyethylene glycol and/or polypropylene glycol has a weight average molecular weight ($M_w$) of about 300.

Embodiment Q. The topical anesthetic composition according to any one of Embodiments A, B, C, D, E, F, G, H, I, J, K, L, M, N, O, or P, wherein the component D is polyethylene glycol.

Embodiment R. The topical anesthetic composition according to any one of
Embodiments A, B, C, D, E, F, G, H, I, J, K, L, M, N, P, or Q, which has a maximum viscosity of about 25 centipoise and a pH of about 6.2 to about 7.4.

Embodiment S. The topical anesthetic composition according to any one of Embodiments A, B, or C, wherein A. is benzocaine; B is tetracaine hydrochloride; the amount of ethanol is 12% by weight; D. is PEG 300; the amount of the propylene glycol is 17% by weight; and the amount of water is about 18% by weight.

Embodiment T. The topical anesthetic composition according to any one of Embodiments A, B, or C, wherein A. is benzocaine; B is tetracaine hydrochloride; the amount of ethanol is 10% by weight; D is PEG 300; the amount of the propylene glycol is 19% by weight; and the amount of water is about 18% by weight.

Embodiment U. The topical anesthetic composition according to any one of Embodiments A, B, or C, wherein A. is benzocaine; B is tetracaine hydrochloride; the amount of ethanol is 10% by weight; D is PEG 300; the amount of the propylene glycol is 17% by weight; and the amount of water is about 20% by weight.

Embodiment V. The topical anesthetic composition according to any one of Embodiments A, B, or C, wherein A. is benzocaine; B is tetracaine hydrochloride; the amount of ethanol is 10% by weight; D is PEG 300; the amount of the propylene glycol is 14% by weight; and the amount of water is about 23% by weight.

Embodiment W. The topical anesthetic composition according to any one of Embodiments A, B, C, D, E, F, G, H, I, J, K, L, M, N, O, P, Q, R, S, T, U, or V, which further comprises benzalkonium chloride.

Embodiment X. The topical anesthetic composition according to any one of Embodiments A, B, C, D, E, F, G, H, I, J, K, L, M, N, O, P, Q, R, S, T, U, V, or W, which further comprises sodium saccharide and/or a flavorant.

Embodiment Y. A method for dispensing the topical anesthetic composition according to any one of any one of Embodiments A, B, C, D, E, F, G, H, I, J, K, L, M, N, O, P, Q, R, S, T, U, V, W, or X, to a desired site by spraying the topical anesthetic from a pump actuated metered dose spray device.

Embodiment Z. A method for dispensing the topical anesthetic composition according to any one of any one of Embodiments A, B, C, D, E, F, G, H, I, J, K, L, M, N, O, P, Q, R, S, T, U, V, W, or X, to a desired site subgingivally with a syringe and applicator tip.

Embodiment AA. A product comprising the topical anesthetic composition according to any one of any one of Embodiments A, B, C, D, E, F, G, H, I, J, K, L, M, N, O, P, Q, R, S, T, U, V, or W, contained in a pump actuated metered dose spray device.

The foregoing description of the invention illustrates and describes the present disclosure.

Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

The term "comprising" (and its grammatical variations) as used herein is used in the inclusive sense of "having" or "including" and not in the exclusive sense of "consisting only of". All publications, patents and patent applications cited in this specification are herein incorporated by reference, and for any and all purposes, as if each individual publication, patent or patent application were specifically and individually indicates to be incorporated by reference. In the case of inconsistencies, the present disclosure will prevail.

What is claimed is:

1. A topical anesthetic composition comprising:
   A. benzocaine, pharmaceutically acceptable salt thereof, amide thereof and/or ester thereof in an amount of about 10% to about 20% by weight;
   B. tetracaine and/or pharmaceutically acceptable salt thereof in an amount of about 1% to about 5% by weight;
   C. ethanol in an amount of about 5% to about 20% by weight;
   D. polyethylene glycol and/or polypropylene glycol in an amount of about 20 to about 35% by weight;
   E. propylene glycol in an amount of about 10% to about 30% by weight;
   F. water in an amount of about 5% to about 30% by weight; and
   G. benzyl alcohol in an amount of about 1% to about 10% by weight;
   and the amounts of A to G are based upon the total amount of A to G in the composition, and wherein said topical anesthetic composition has a maximum viscosity of about 25 centipoise, as determined by using a TA Instrument Advanced Rheometer AR1000 Stress controlled rheometer with viscosity measurements made using a 60 mm acrylic plate geometry at a 1000 µm gap, and a set temperature of 25° C. against increasing applied shear stress from 0.01-50 Pa.

2. The topical anesthetic composition according to claim 1, wherein the amount of the benzocaine, pharmaceutically acceptable salt thereof, amide thereof and/or ester thereof is about 14% by weight.

3. The topical anesthetic composition according to claim 1, wherein the amount of the tetracaine and/or pharmaceutically acceptable salt thereof is about 2% by weight.

4. The topical anesthetic composition according to claim 1, wherein the amount of the ethanol is about 10% to about 15% by weight.

5. The topical anesthetic composition according to claim 1, wherein the amount of the ethanol is about 10% to about 12% by weight.

6. The topical anesthetic composition according to claim 1, wherein the amount of the polyethylene glycol and/or polypropylene glycol is about 25% to about 30% by weight.

7. The topical anesthetic composition according to claim 1, wherein the amount of the polyethylene glycol and/or polypropylene glycol is about 29% to about 30% by weight.

8. The topical anesthetic composition according to claim 1, wherein the amount of the propylene glycol is about 10% to about 25% by weight.

9. The topical anesthetic composition according to claim 1, wherein the amount of the propylene glycol is about 13% to about 22.5% by weight.

10. The topical anesthetic composition according to claim 1, wherein the amount of the amount of the water is about 10% to about 25% by weight.

11. The topical anesthetic composition according to claim 1, wherein the amount of the amount of the water is about 15% to about 23.5% by weight.

12. The topical anesthetic composition according to claim 1, wherein the amount of the amount of the benzyl alcohol is about 5% by weight.

13. A topical anesthetic composition comprising
   A. benzocaine, pharmaceutically acceptable salt thereof, amide thereof and/or ester thereof in an amount of about 14% by weight;
   B. tetracaine and/or pharmaceutically acceptable salt thereof in an amount of about 2% by weight;
   C. ethanol in an amount of about 10 to about 12% by weight;
   D. polyethylene glycol and/or polypropylene glycol in an amount of about 29 to about 30% by weight;
   E. propylene glycol in an amount of about 13 to about 22.5% by weight;
   F. water in an amount of about 15 to about 23.5% by weight; and
   G. benzyl alcohol in an amount of about 5% by weight
   the amounts of A to G are based upon the total amount of A to G in the composition, and wherein said topical anesthetic composition has a maximum viscosity of about 25 centipoise, as determined by using a TA Instrument Advanced Rheometer AR1000 Stress controlled rheometer with viscosity measurements made using a 60 mm acrylic plate geometry at a 1000 µm gap, and a set temperature of 25° C. against increasing applied shear stress from 0.01-50 Pa.

14. The topical anesthetic composition according to claim 1, wherein the polyethylene glycol and/or polypropylene glycol has a weight average molecular weight ($M_w$) of at least about 100.

15. The topical anesthetic composition according to any one of claim 1, 2, 3, 4, 5, 6, 7, 8, or 13, wherein the polyethylene glycol and/or polypropylene glycol has a weight average molecular weight ($M_w$) of about 100 to about 700.

16. The topical anesthetic composition according to claim 1, wherein the polyethylene glycol and/or polypropylene glycol has a weight average molecular weight ($M_w$) of about 300.

17. The topical anesthetic composition according to claim 1, wherein the component D is polyethylene glycol.

18. The topical anesthetic composition according to claim 1, which has a pH of about 6.2 to about 7.4.

19. The topical anesthetic composition according to claim 1, wherein A. is benzocaine; B is tetracaine hydrochloride;

the amount of ethanol is 12% by weight; D is PEG 300; the amount of the propylene glycol is 17% by weight; and the amount of water is about 18% by weight.

20. The topical anesthetic composition according to claim 1, wherein A. is benzocaine; B is tetracaine hydrochloride; the amount of ethanol is 10% by weight; D is PEG 300; the amount of the propylene glycol is 19% by weight; and the amount of water is about 18% by weight.

21. The topical anesthetic composition according to claim 1, wherein A. is benzocaine; B is tetracaine hydrochloride; the amount of ethanol is 10% by weight; D is PEG 300; the amount of the propylene glycol is 17% by weight; and the amount of water is about 20% by weight.

22. The topical anesthetic composition according to claim 1, wherein A. is benzocaine; B is tetracaine hydrochloride; the amount of ethanol is 10% by weight; D is PEG 300; the amount of the propylene glycol is 14% by weight; and the amount of water is about 23% by weight.

23. The topical anesthetic composition according to claim 1, which further comprises benzalkonium chloride.

24. The topical anesthetic composition according to claim 1, which further comprises sodium saccharide and/or a flavorant.

25. A method for dispensing the topical anesthetic composition according to claim 1, to a desired site by spraying the topical anesthetic from a pump actuated metered dose spray device.

26. A method for dispensing the topical anesthetic composition according to claim 1, to a desired site subgingivally with a syringe and applicator tip.

27. A product comprising the topical anesthetic composition according to claim 1, contained in a pump actuated metered dose spray device.

28. The topical anesthetic composition according to claim 1, wherein the maximum viscosity is about 20 centipoise.

29. The topical anesthetic composition according to claim 1, wherein the maximum viscosity of about 15 centipoise.

30. The topical anesthetic composition according to claim 1, which contains less than 0.1% by weight of dipropylene glycol.

31. The topical anesthetic composition according to claim 1, being a spray composition not containing a propellant.

* * * * *